United States Patent [19]

Steen

[11] 4,141,238
[45] Feb. 27, 1979

[54] METHOD FOR THE DETERMINATION OF THE AMOUNT OF PARTICLES IN GASEOUS MEDIA AND A SAMPLING DEVICE FOR PERFORMING THE METHOD

[75] Inventor: Bengt Steen, Gothenburg, Sweden

[73] Assignee: Institutet för Vatten- och Luftvårdsforskning, Stockholm, Sweden

[21] Appl. No.: 786,366

[22] Filed: Apr. 11, 1977

[30] Foreign Application Priority Data

Apr. 15, 1976 [SE] Sweden .............................. 7604454

[51] Int. Cl.² .......................... G01N 15/00; G01N 1/22
[52] U.S. Cl. .................................. 73/28; 73/421.5 R
[58] Field of Search ............................. 73/28, 421.5 R

[56] References Cited

U.S. PATENT DOCUMENTS

| | | | |
|---|---|---|---|
| 2,281,962 | 5/1942 | Tongeren | 73/28 X |
| 2,857,978 | 10/1958 | Lenger | 73/28 X |
| 3,774,442 | 11/1973 | Gustavsson | 73/28 |
| 3,784,902 | 1/1974 | Huber | 73/28 |

FOREIGN PATENT DOCUMENTS 913231  5/1946  France .......................... 73/28

*Primary Examiner*—S. Clement Swisher
*Attorney, Agent, or Firm*—Holman & Stern

[57] ABSTRACT

In establishing the rate of air pollution is required a simple method and apparatus for determining the amount of particles in a gaseous medium.

This is achieved with a tube-shaped sampler provided with means for establishing an isokinetic flow therethrough and having a high-tension connected rod-formed emission electrode disposed therein in insulated relationship relative to said tube, said tube being connected to ground for establishing a force of field giving the tube a function as collecting electrode.

The sampler is placed in the flow of gas to be determined upon with its longitudinal direction substantially aligned with the flow direction. The particles collected in the sampler tube during a predetermined time is weighed and the result is possibly related to the difference in areas between sampler and gas flow for establishing the mass of particles per unit of time.

3 Claims, 5 Drawing Figures

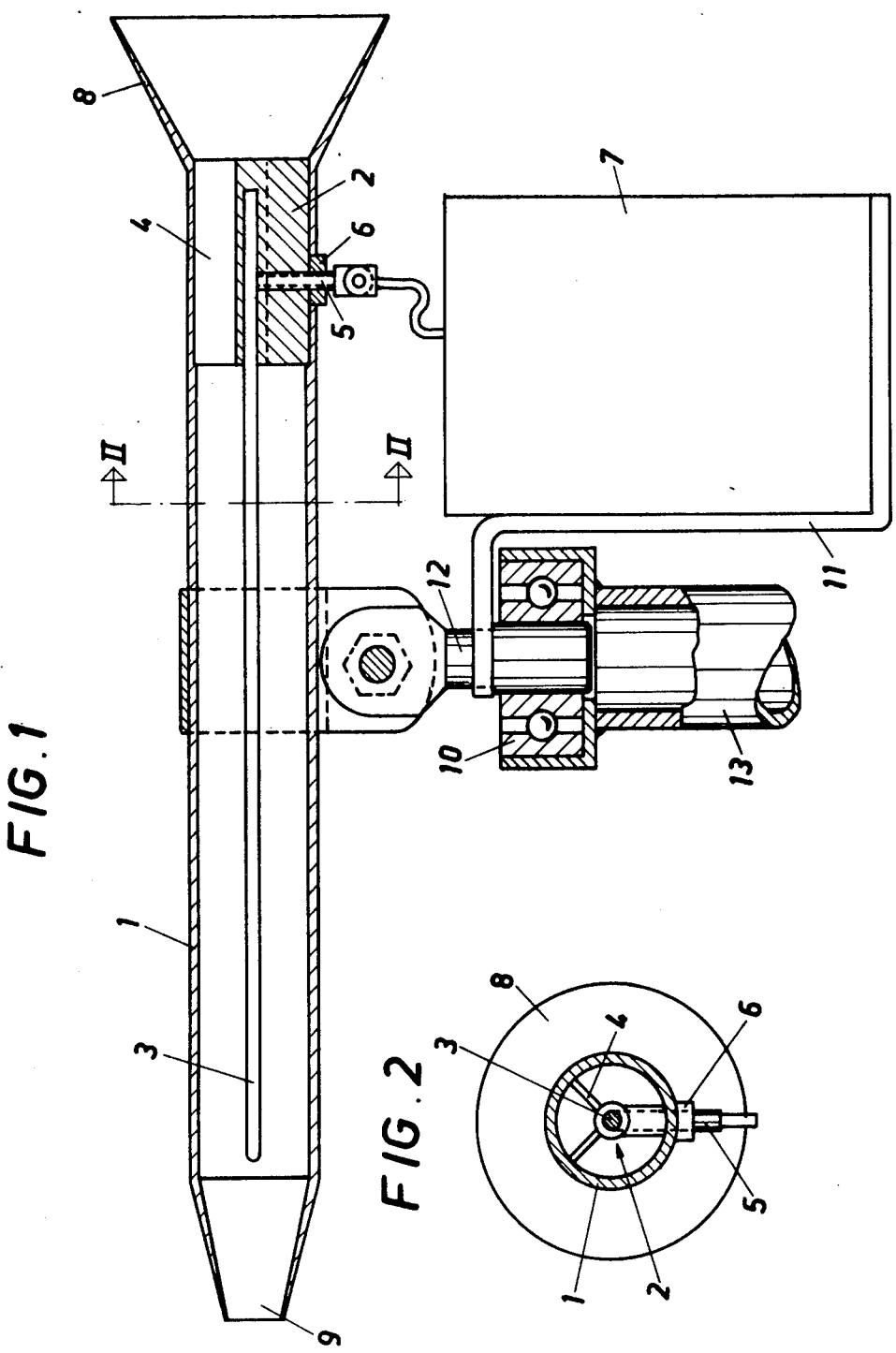

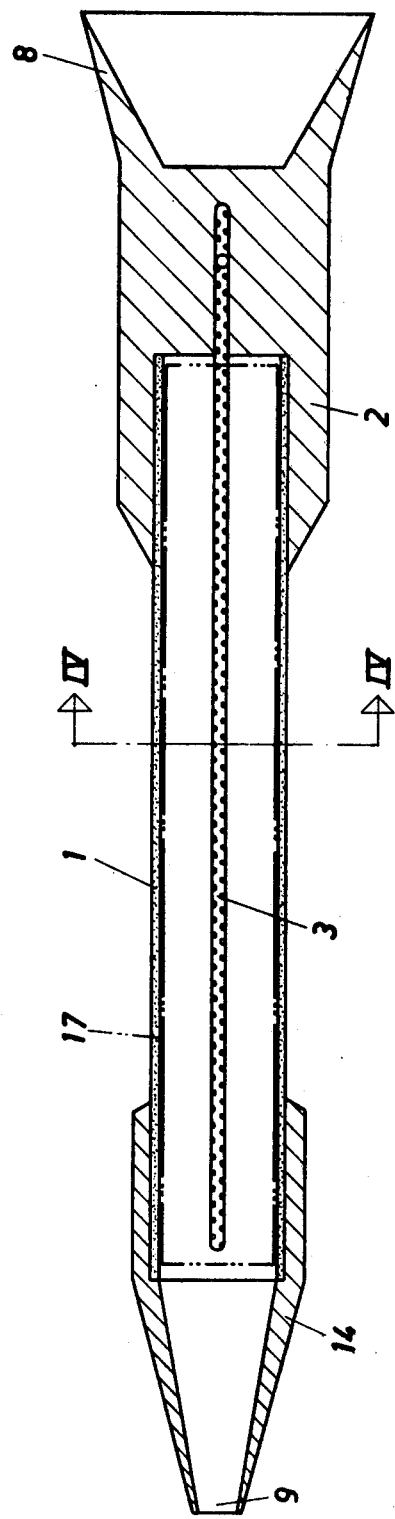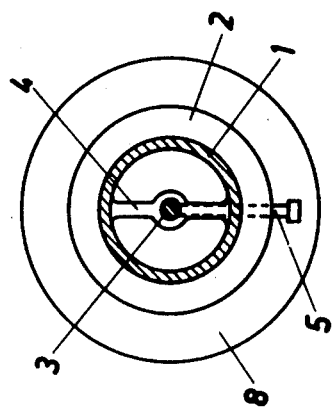

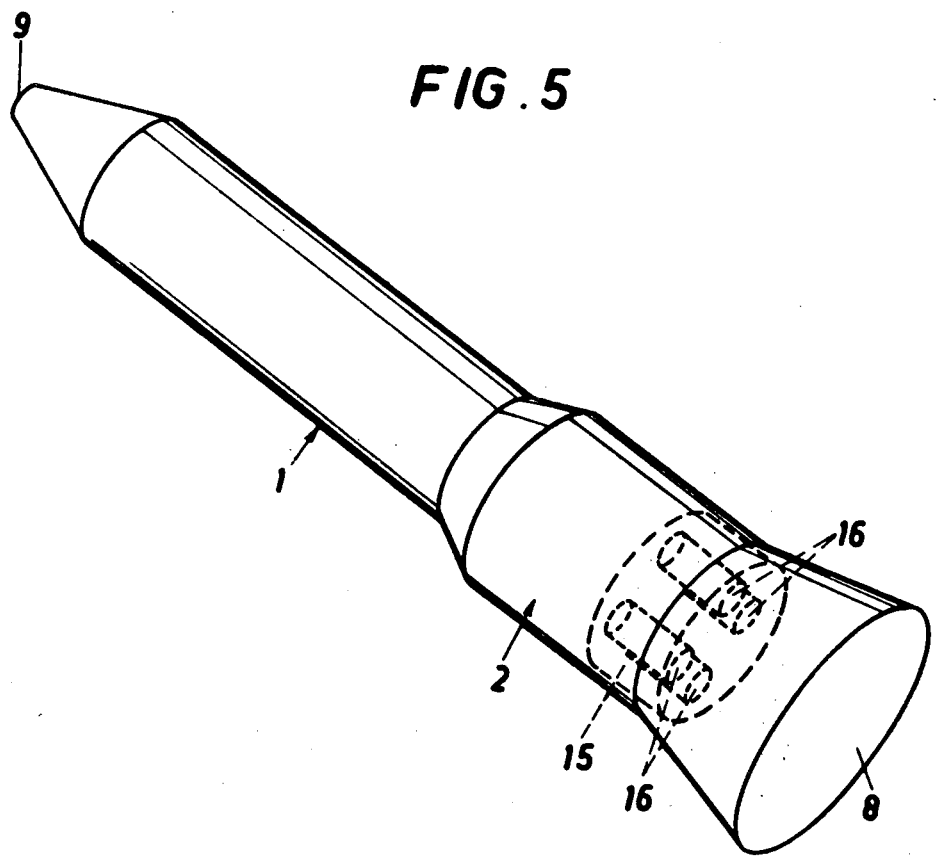

METHOD FOR THE DETERMINATION OF THE AMOUNT OF PARTICLES IN GASEOUS MEDIA AND A SAMPLING DEVICE FOR PERFORMING THE METHOD

BACKGROUND OF THE INVENTION

The present invention refers to a method for determination of the amount of particles in gaseous media and a sampling device for performing the method.

In air conservation there is a large need for a simple method of measuring the amount of particles transported in gaseous media, e.g. in connection to discharge of pollution (emission) or a particle transport (mass per unit of time and surface) to a receiver (immission).

The measuring of particle emission in stacks and flues has hitherto mainly been carried out with use of manual methods. At such a measurement is on one hand the gas flow determined and on the other hand the mass concentration upon an isokinetic sampling on filters. The measurements require some calculations during and after the very sampling operation, whereby an especially trained staff is needed for these measurements. The performing of such a measurement requires a large number of filters, a comprehensive equipment for flow control for guaranteing isokinetic sampling and a particular system for gas flow determination. Each measurement requires the work of several men and it is thus very expensive as well regarding working as equipment costs.

A system for emission measurement in skylight turrets has earlier been developed in the USA and this system is based on so called "High Volume Samplers", but the sampling is in that case not made isokinetically whereby the accuracy of measurement is lower. The costs for the measuring equipment and the measuring work is also in this case very high.

Alternative methods for the measuring of immissions are based on a measurement of a mean concentration per unit of time and a mean wind velocity. If there is a correlation between the wind velocity and the concentration will here a systematic error in measurement be obtained. (A comparatively large number of samples are taken at low wind velocities when the immission is small and vice versa). A systematic error of measurement is also got as the sampling is generally brought about non-isokinetically.

SUMMARY OF THE INVENTION

The purpose of the present invention is to provide a method and a sampling device, which is characterized by a large accuracy of measurement, which is nonexpensive to acquire and which for each measurement requires very little work, whereby the complete measurement cost will be low. The measurement equipment must furthermore be simple to use and it must not require any especially trained personnel. These tasks have been solved by the invention thereby that at least one cylindrical sleeve, which is open at both ends is placed into and in parallel to a flow of gas that at least one emission electrode which is arranged in said sleeve is connected to a high-tension source, which charges the particles or dust contained in the gas, that the sleeve is earthed and a field of force is formed between the sleeve and the emission electrode in order to make the particles collect on the sleeve or on a lining disposed therein, and that the amount of particles collected during a predetermined period of time is related to the nozzle area of the said sleeve.

BRIEF DESCRIPTION OF DRAWINGS

FIG. 1 shows a longitudinal section through a sampling device according to the invention, FIG. 2 is a section along line II—II in FIG. 1, FIG. 3 shows a longitudinal section through a modified embodiment of the sampling device, FIG. 4 is a section along line IV—IV in FIG. 3, FIG. 5 shows in a perspective elevation a further embodiment of the sampling device.

DESCRIPTION OF THE PREFERRED EMBODIMENTS

The sampling device comprises a cylindrical sleeve 1, which is open at both ends and which at one of its ends is provided with a retainer 2 for an emission electrode 3. This emission electrode is arranged concentrically in the sleeve and it extends through a substantial portion thereof. The retainer is made of a dielectric material and it is designed in such a manner that it will reduce the cross sectional area of the sleeve so little as possible. In the embodiment shown comprises the retainer a central portion from which three spacing members 4 project and these spacing members engage against the inner side of the sleeve. Inside one of the spacing members 4 is arranged a screw 5 by means of which the electrode 3 can be locked to the retainer and this screw 5 furthermore forms the external current supplying connection of the electrode. In order to make sure that the screw shall not come into contact with the sleeve 1 is an insulator 6 arranged in the sleeve. The electrode 3 is connected to a high-tension generator 7, which comprises a D.C. source, e.g. a number of flash light batteries, an oscillator transformer and a voltage multiplier by means of which the D.C. current of the batteries of for instance six volts is transformed to a D.C. current of for instance 15,000 V at 1 $\mu$A. The sampling device is connected in such a manner to the earth connection of the D.C. source that the sleeve 1 will work as a collecting electrode.

In order to compensate for the pressure drop and thereby the somewhat lower gas velocity caused by friction between the gas and the cylinder walls and the emission electrode with retainer has the rear end of the cylinder, as seen in the direction of flow, been designed with an expanded portion 8, whereby the gas flow lines on the outside of the sleeve are "pressed" together and the outer gas velocity at the rear end of the sleeve will increase. This gives a subpressure at the expanded portion 8 of the sleeve, and the taper of said portion is for this reason chosen in such a manner that the subpressure will compensate the pressure drop caused by the friction and maintain an isokinetic sampling.

The sleeve 1 can preferably be provided with a constricted opening 9 at its front end as seen in the direction of flow in order to allow an increased dwelling time for the particles which pass the opening and it is thereby brought about an increased ratio of separation and an increased capacity of the sampling device concerning separated particles.

In such cases where the sampling device shall be used for outdoor measurements, i.e. in the ambient atmosphere the sampling device is preferably journalled in a ball bearing 10 or the like and it is possibly provided with a fin (not shown) to make the sampling device wind-controlled in such a manner that the sampling inlet all the time is facing the wind. The high-tension generator 7 is in this case carried by a bracket 11, which is non-rotatably connected to the rotational trunnion 12 of the sampling device to allow the generator to take part in the wind controlled rotational movement. The journal of the sampling device is carried in a frame, a tower or another suitable fixture, which makes it possible to locate the device in different positions.

The embodiment shown in FIGS. 3 and 4 differ from the above mentioned embodiment in that the retainer 2 for the emission electrode is designed to form the rear expanded portion 8 of the sampling device. Another difference as compared to the first embodiment is that the constricted opening is arranged in a tapering nozzle, which can be pushed onto the front end of the sleeve. An advantage with this arrangement is that the nozzle 14 and the retainer 2 with the expanded portion 8 and the passages in this portion are exchangeable for corresponding members having a larger or smaller opening 9, through-flow passages and a varying taper of portion 8. In FIG. 5 is illustrated that the retainer 2 can be provided with a fixed or detachable throttle washer 15 provided with a number of passages 16. By using throttle washers having different passage areas is it possible to provide accurate isokinetic sampling conditions.

The material in sleeve 1, which acts as a collector electrode is preferably aluminum, or, when the device shall be used in corrosive environments, stainless steel. It can in some cases be expedient to locate a metal foil or a very thin cylinder in the sleeve such as shown with dash and dot lines in FIG. 3. A detachable foil or a cylindric lining will make the handling of the samples easier. The mass determination of the particles can for instance be performed by weighing.

The measurement of the particle mass in gaseous media is brought about in the following manner.

The sleeve 1 which is open at both ends is placed into and in parallel with a gas flow and the emission electrode 3, which is located in the retainer 2 is connected to a high-tension generator 7, which will give such a high tensioned D.C. current that the corona limit is exceeded. As the sleeve is earthed will it act as a collector electrode and a field of force is formed between the sleeve and the emission electrode 3 to make the particles in the gas collect on the inner side of the sleeve. The mass of particles separated during a predetermined period of time are weighed and the result may possibly be related to the gas volume, which during the same period of time has passed through the sleeve. If the sampling for instance are brought about in a stack is the separated particle mass value multiplited by a constant which will define the relation between the stack area and the nozzle area of the sampling device in order to obtain the entire emission during the sampling time.

With the sampling device according to the invention is it possible to measure as well diffuse emissions of particles from stock yards and the like and also emissions from skylight turrets, windows or the like and in flues, but it is also possible to measure immissions for instance in form of particles transported over the borders of a land area.

The invention is not limited to the described and shown embodiments but a plurality of variations are possible within the scope of the appended claims. The expression "particles" in this context is intended to mean as well solid as liquid particles.

What I claim is:

1. An apparatus for the isokinetic sampling of the amount of particles transported by a gaseous media, said apparatus comprising:
    a cylindrical sleeve having an inner surface;
    an electrode concentrically disposed in said sleeve;
    an insulator for mounting said electrode in said sleeve and insulating said electrode from said sleeve;
    voltage means for charging said electrode to a high voltage with respect to said sleeve; and
    gas supply means for providing isokinetic gas flow through said sleeve, wherein said particles are charged and attracted to the inner surface of said sleeve, wherein said gas supply means comprises a rear end of said sleeve, as seen in the direction of flow, and has an expanded portion.

2. A sampling device as claimed in claim 3, wherein said expanded portion forms part of said insulator.

3. A sampling device for the determination of the amount of particles transported in a gaseous medium, characterized by, a cylindrical sleeve open at both ends and having at the rear end thereof a means for establishing isokinetic gas flow therethrough comprising a conically expanded end portion and at its opposite, front end a constricted nozzle portion, at least one rod formed emission electrode disposed concentric in said sleeve, a retainer connected to said sleeve in electrically insulated relation thereto, said retainer being arranged to carry said emission electrode, a high tension generator connected to said emission electrode and an earth connection connected to said sleeve to make this sleeve act as a collector electrode.

* * * * *